(12) United States Patent
Huang et al.

(10) Patent No.: US 10,004,461 B2
(45) Date of Patent: Jun. 26, 2018

(54) PHYSIOLOGICAL SIGNAL PROCESSING SYSTEM AND METHOD FOR FILTERING NOISE GENERATED BY THE SAME

(71) Applicant: AUTOMOTIVE RESEARCH & TESTING CENTER, Lugang Chen, Changhua Hsien (TW)

(72) Inventors: Hsuan-Yu Huang, Changhua Hsien (TW); Yen-Cheng Feng, Changhua Hsien (TW)

(73) Assignee: AUTOMOTIVE RESEARCH & TESTING CENTER, Lugang Chen, Changhua Hsien (TW)

( * ) Notice: Subject to any disclaimer, the term of this patent is extended or adjusted under 35 U.S.C. 154(b) by 275 days.

(21) Appl. No.: 14/984,890

(22) Filed: Dec. 30, 2015

(65) Prior Publication Data
US 2017/0188970 A1   Jul. 6, 2017

(51) Int. Cl.
*A61B 5/00* (2006.01)
*A61B 5/024* (2006.01)
*A61B 5/18* (2006.01)
*A61B 5/11* (2006.01)

(52) U.S. Cl.
CPC .......... *A61B 5/7207* (2013.01); *A61B 5/0002* (2013.01); *A61B 5/02405* (2013.01); *A61B 5/02416* (2013.01); *A61B 5/11* (2013.01); *A61B 5/18* (2013.01); *A61B 5/681* (2013.01); *A61B 5/7221* (2013.01)

(58) Field of Classification Search
CPC ... A61B 5/0205; A61B 5/7214; A61B 5/7203; A61B 5/725; A61B 5/7264
See application file for complete search history.

(56) References Cited

U.S. PATENT DOCUMENTS

| 2011/0213271 A1* | 9/2011 | Telfort | A61B 7/003 600/586 |
| 2012/0022336 A1* | 1/2012 | Teixeira | A61B 5/0205 600/300 |
| 2012/0022844 A1* | 1/2012 | Teixeira | A61B 5/0205 703/11 |
| 2014/0142395 A1* | 5/2014 | Sattler | A61B 5/7203 600/300 |

(Continued)

FOREIGN PATENT DOCUMENTS

TW   201511735 A   4/2015

*Primary Examiner* — Jaehwan Oh
(74) *Attorney, Agent, or Firm* — patenttm.us

(57) ABSTRACT

A physiological signal processing method for filtering noise generated by a physiological signal processing system is performed by a physiological signal processing system having a sensing device and a filtering device in connection with the sensing device. The method comprises steps of synchronously receiving a physiological signal and a vibrational signal detected by the sensing device, performing a noise determination algorithm to acquire information in multiple time periods with noises occurring in corresponding time periods according to the vibrational signal, performing a physiological signal filtering algorithm to filter the noises in corresponding time periods of the physiological signal and compensate the filtered physiological signal, and estimating a physiological parameter according to a result of the signal compensation to generate the physiological parameter with accuracy.

9 Claims, 9 Drawing Sheets

(56) References Cited

U.S. PATENT DOCUMENTS

2014/0275886 A1* 9/2014 Teixeira ............... A61B 5/0205
600/324
2016/0262687 A1* 9/2016 Vaidyanathan ...... A61B 5/7264

* cited by examiner

PHYSIOLOGICAL SIGNAL PROCESSING SYSTEM AND METHOD FOR FILTERING NOISE GENERATED BY THE SAME

BACKGROUND OF THE INVENTION

1. Field of the Invention

The present invention relates to a signal processing system and a signal processing method and, more particularly, to a physiological signal processing system and a method for filtering noise generated by the same.

2. Description of the Related Art

Because of rapid technological advancement, some physiological states of human body can be analyzed and monitored through wearable devices, which are oftentimes applied to areas of exercise, medical treatment, sleep and car driving. For example, when a user wears a smart watch equipped with optical sensors, the smart watch senses user's activities upon exercising or walking, detects user's physiological signals, such as photoplethysmogram (PPG) signals, and analyzes the physiological signals to acquire physiological parameters in association with user's heart rate variability (HRV). The more correct the acquired physiological signals are, the more accurate the user's HRV is.

When conventional smart watches are used to monitor users' PPG signals, optical leakage easily arises from vibration, noise and users' body movement and causes distorted PPG signals, rendering the PPG signals inaccurate. Moreover, PPG signals tend to have large quantity of data and conventional methods for analyzing PPG signals are too complicated and time-consuming to achieve real time processing of PPG signals. As disclosed in Taiwan patent publication no. 201511735, entitled "A PPG-based physiological sensing system with spatio-temporal sampling approach toward identifying and removing motion artifacts from optical signal" (hereinafter "the conventional system"), the PPG-based physiological sensing system is mainly applied to technical fields of fitness and/or exercise to realize stabilization and accurate determination of PPG signals. According to the PPG-based physiological sensing system, a spatio-temporal sampling approach toward identifying and removing motion artifacts from optical signal is employed. During each state of body movement, the optical signal can be instantaneously received by a wearable optical sensing device. The techniques available to digital signal processing for the conventional system include Kalman filter, Fourier analysis, peak value identification and independent component analysis (ICA). The optical signals received over time are processed to identify and remove motion artifacts from the optical signals, such that the physiological parameters can be accurately determined to restore the real PPG signals and inaccuracy resulting from motion artifacts in the physiological sensing device can be resolved.

As can be seen from the foregoing conventional system, wearable devices can be used to monitor users' physiological signals. Higher accuracy of acquired physiological signals ensures more correct determination of users' physiological states. Upon detection of users' physiological signals, physiological signals are prone to distortion because of vibration, noise and users' body movement. In view of large quantity of data, enhanced accuracy of physiological signals requires time-consuming analysis and computations. Despite a bunch of digital signal processing techniques for improvement of signal accuracy, complicated mathematical analysis method is not only time-consuming but also fails to meet the demand of instant processing. Especially for vehicle driving, if intending to get rid of noise for signal restoration using complicated digital signal processor, it is impossible to attain instant physiological analysis of drivers for the sake of long computation time required.

SUMMARY OF THE INVENTION

An objective of the present invention is to provide a physiological signal processing system and a method for filtering noises generated by the same, which utilizes instant and high-speed signal processing techniques to lower computation time of the system and filter out noises in a physiological signal detected by the physiological signal processing system, thereby enhancing accuracy of the detected physiological signals.

To achieve the foregoing objective, the method for filtering the noise generated by a physiological signal system having a sensing device and a filtering device in connection with the sensing device is performed by the filtering device and includes steps of:

synchronously receiving a physiological signal and a vibrational signal detected by the sensing device;

performing a noise determination algorithm to acquire information over time associated with the vibrational signal with noises occurring in corresponding time periods of the vibrational signal;

performing a physiological signal filtering algorithm to filter out portions with noises in the corresponding time periods of the physiological signal and compensate the filtered physiological signal; and estimating the compensated physiological signal to generate a physiological parameter according to a result of the signal compensation.

Given the foregoing method, when a user wears the sensing device, the sensing device transmits the detected physiological signal and the vibrational signal to the filtering device installed in a vehicle for the filtering device to perform the noise determination algorithm to acquire the information over time associated with the vibrational signal with noises occurring in corresponding time periods of the vibrational signal, and then performs the physiological signal filtering algorithm to filter out the noises in the corresponding time periods of the physiological signal, compensates the filtered physiological signal to reduce errors arising from the noises during estimation of the physiological signal, and estimates the compensated physiological signal to generate a physiological parameter according to the result of the signal compensation. Accordingly, regardless of whether the vehicle is moving or stopped, the information of the corresponding time periods in the vibrational signal can be acquired through the noise determination algorithm and the noises in the physiological signal can be filtered out to provide accurate physiological signals.

To achieve the foregoing objective, a physiological signal processing system includes a sensing device and a filtering device.

The sensing device serves to synchronously detect a physiological signal and a vibrational signal.

The filtering device is connected to the sensing device and has a processor performing the method for filtering the noises generated by the physiological signal processing system as described in the foregoing method.

From the foregoing structures, the processor receives a physiological signal and a vibrational signal to perform the noise determination algorithm so as to acquire the information in the corresponding time periods representing noises occurring in the vibrational signal, and then performs the physiological signal filtering algorithm to filter out the noises in the corresponding time periods of the physiological signal, compensates the filtered physiological signal, and estimates the compensated physiological signal to generate a physiological parameter indicative of a physiological state of the user according to the result of the signal compensation. Accordingly, regardless of whether the user is driving or moving, timing of noises can be identified through the noise determination algorithm and the noises in the physiological signal can be filtered out, thereby enhancing accuracy of physiological signals.

Other objectives, advantages and novel features of the invention will become more apparent from the following detailed description when taken in conjunction with the accompanying drawings.

DETAILED DESCRIPTION OF THE INVENTION

It is noted that coordinates of all waveform diagrams in association with FIGS. 3-6 are represented by signal intensity along the vertical direction and time along the horizontal direction, and units of the signal intensity and time are dB (Decibel) and second respectively.

Figure 1:
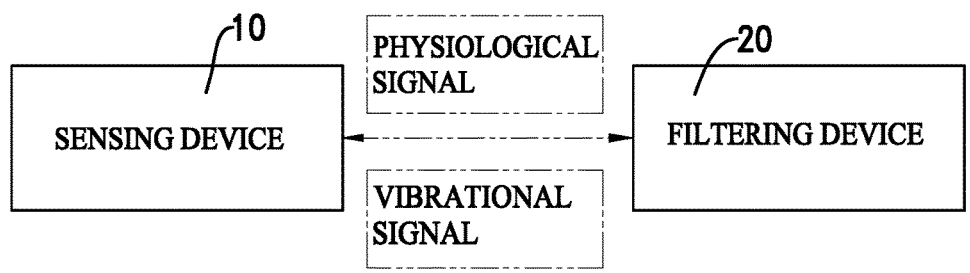
FIG. 1 is a functional block diagram of a physiological signal processing system in accordance with the present invention.

With reference to FIG. 1, a physiological signal processing system in accordance with present invention includes a sensing device 10 and a filtering device 20. The sensing device 10 is installed on a user to synchronously detect the user's physiological signals and vibrational signals occurring in the physiological signal processing system. The filtering device 20 is connected to the sensing device 10 by means of wireline connection or wireless connection. The filtering device 20 is connected to the sensing device 10 according to a communication protocol. The communication protocol may be a Bluetooth® protocol, a WiFi® (Wireless Fidelity) protocol or an RFID® (Radio Frequency Identification). The sensing device 10 and the filtering device 20 may be integrated in a wearable device.

The filtering device 20 includes a processor. The sensing device 10 includes a physiological signal detector and a gravity detector. When synchronously receiving a physiological signal and a vibrational signal (noises) sensed by the sensing device 10, the processor of the filtering device 20 first performs a noise determination algorithm to acquire information over time associated with the vibrational signal with noises occurring in corresponding time periods of the vibrational signal, then performs a physiological signal filtering algorithm that filters out noises in the corresponding time periods in the physiological signal, compensates the filtered physiological signal, and estimates the compensated physiological signal to generate a physiological parameter indicative of the user's physiological state according to the result of the signal compensation.

Figure 2:
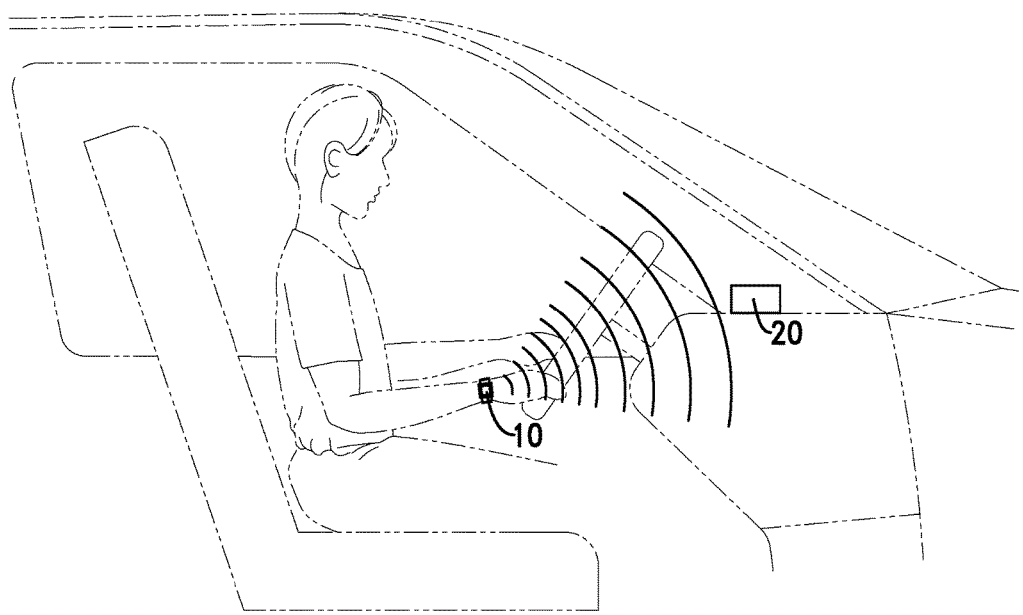
FIG. 2 is an operational schematic view of the physiological signal processing system in FIG. 1.
Figure 3:
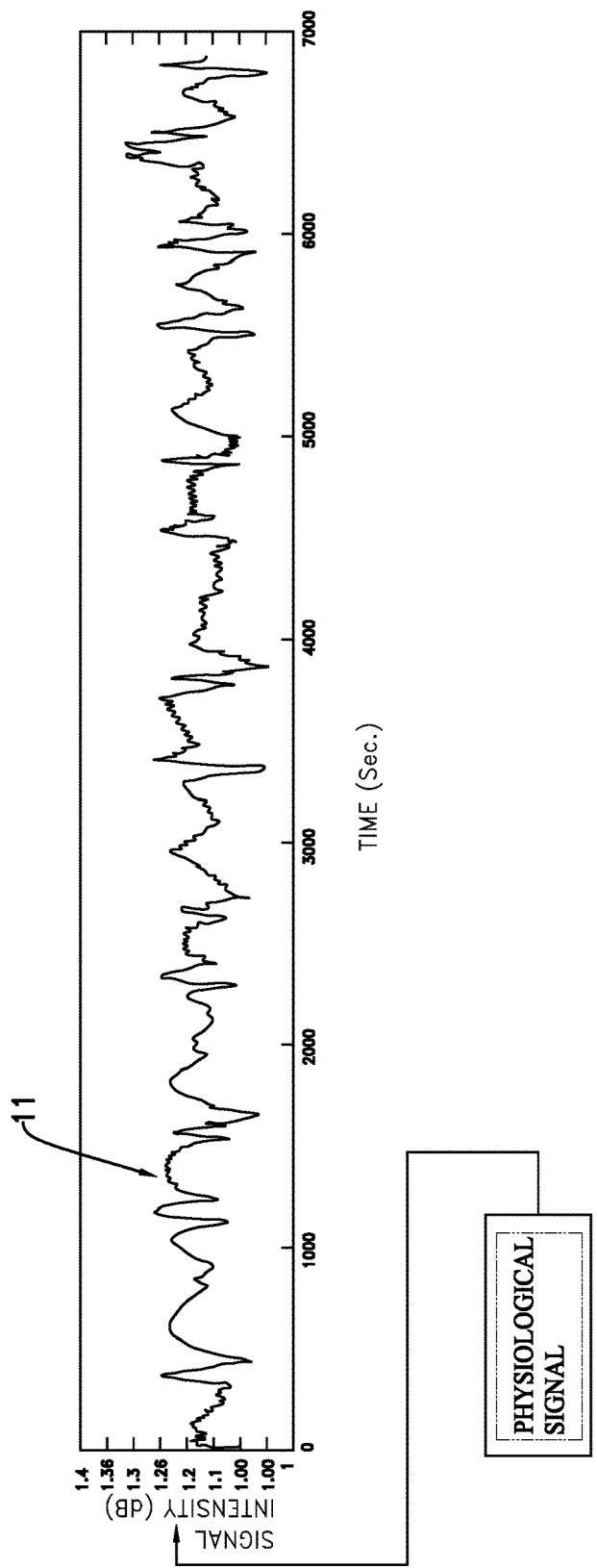
FIG. 3 is a waveform diagram associated with physiological signals generated in the physiological signal processing system in FIG. 1.
Figure 4A:
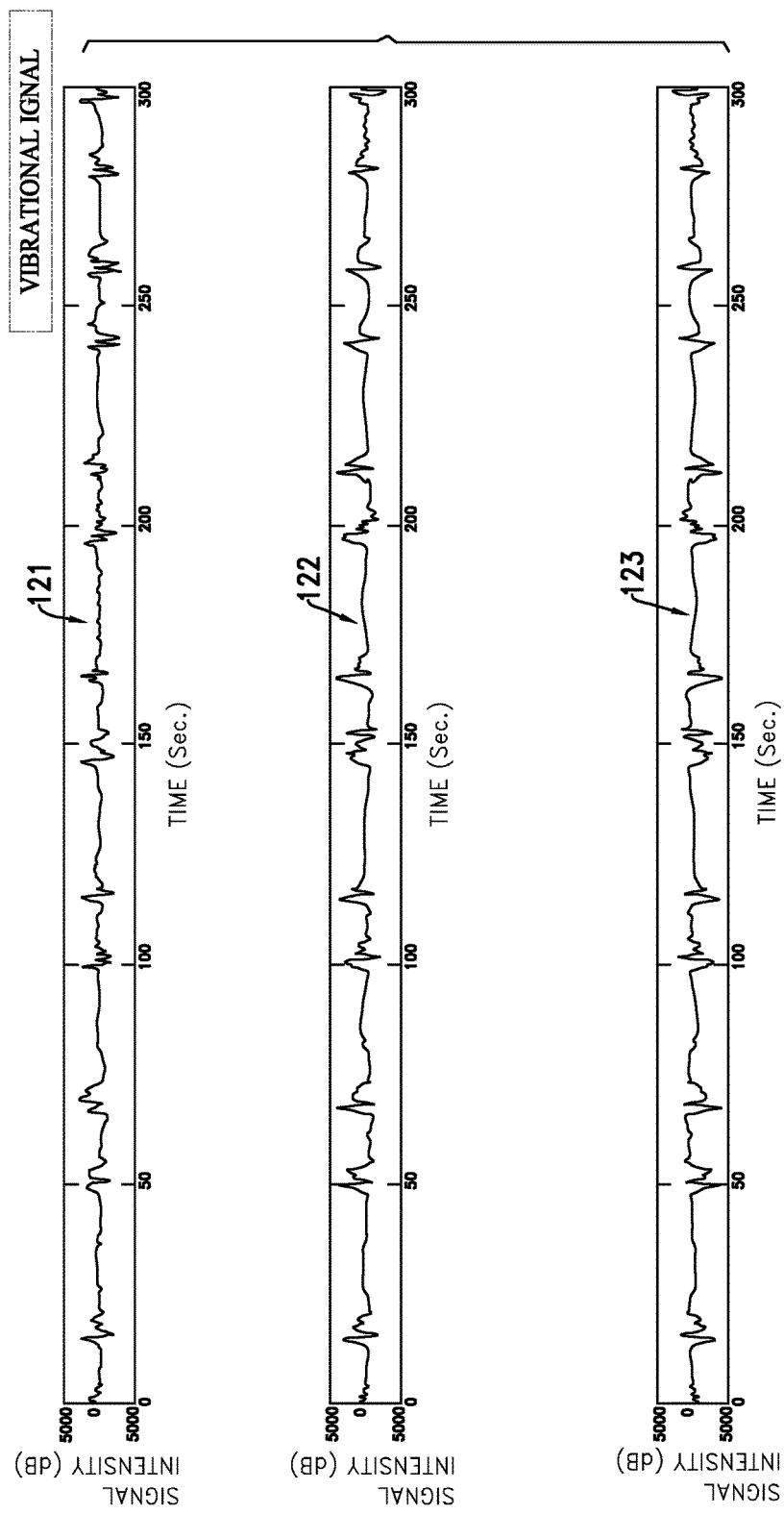
FIG. 4A are waveform diagrams associated with three components of a vibrational signal generated in X, Y and Z axes and occurring in the physiological signal processing system in FIG. 1.
Figure 4B:
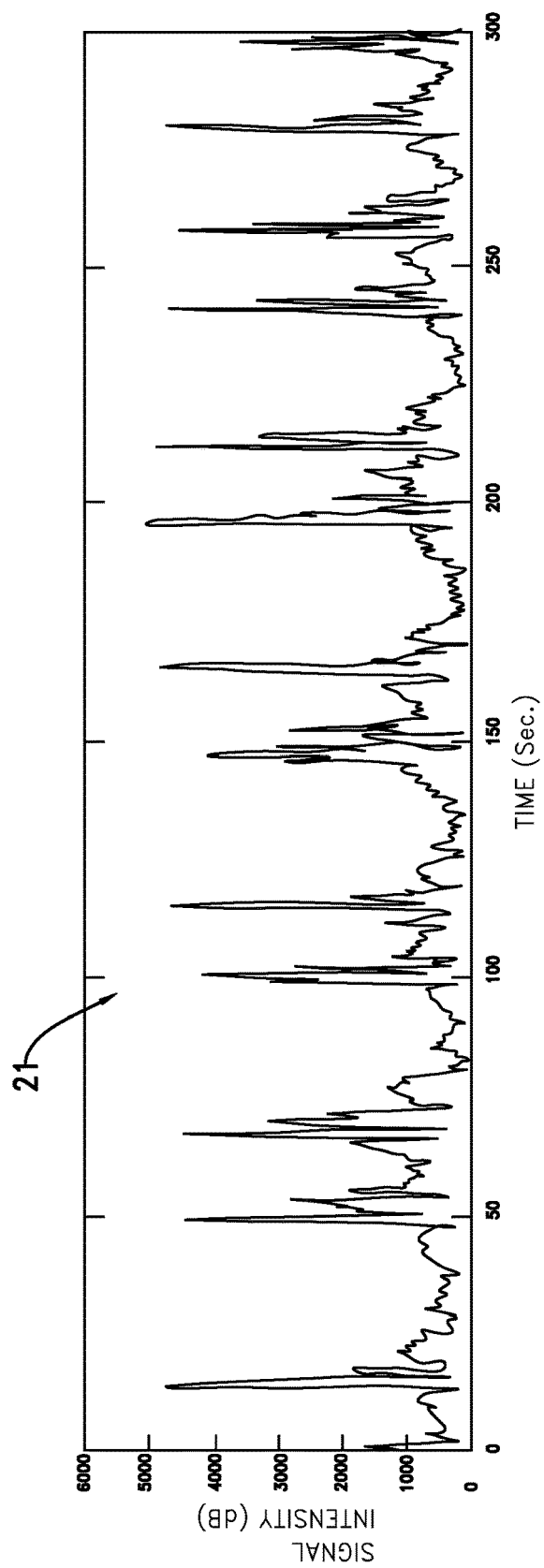
FIG. 4B is a waveform diagram of a resultant vibrational signal from the three components of the vibrational signal in FIG. 4A.

As to implementation of the physiological signal processing system, with reference to FIG. 2, the sensing device 10 may be a wearable smart watch or an optical physiological state detection watch, and the filtering device 20 may be a smart mobile device or a smart vehicular computer. The sensing device 10 is worn around a wrist of a user and the filtering device 20 is installed inside a vehicle. Regardless of whether the vehicle is moving or stopped, the sensing device 10 can constantly monitor physiological signals of the user and vibrational signals. With reference to FIGS. 3, 4A and 4B, the filtering device 20 receives a physiological signal 11 and a vibrational signal 21 transmitted from the sensing device 10 and performs the noise determination algorithm. In the present embodiment, a magnitude of the vibrational signal is calculated by a Z-axis signal 121, a Y-axis signal 122 and an X-axis signal 123 and is expressed by the following equation.

$$G(t) = \sqrt{G_x(t)^2 + G_y(t)^2 + G_z(t)^2}$$

where t represents time;
G(t) represents the vibrational signal 21;
$G_x(t)$ represents the X-axis signal 123;
$G_y(t)$ represents the Y-axis signal 122;
$G_z(t)$ represents the Z-axis signal 121.

Figure 5:
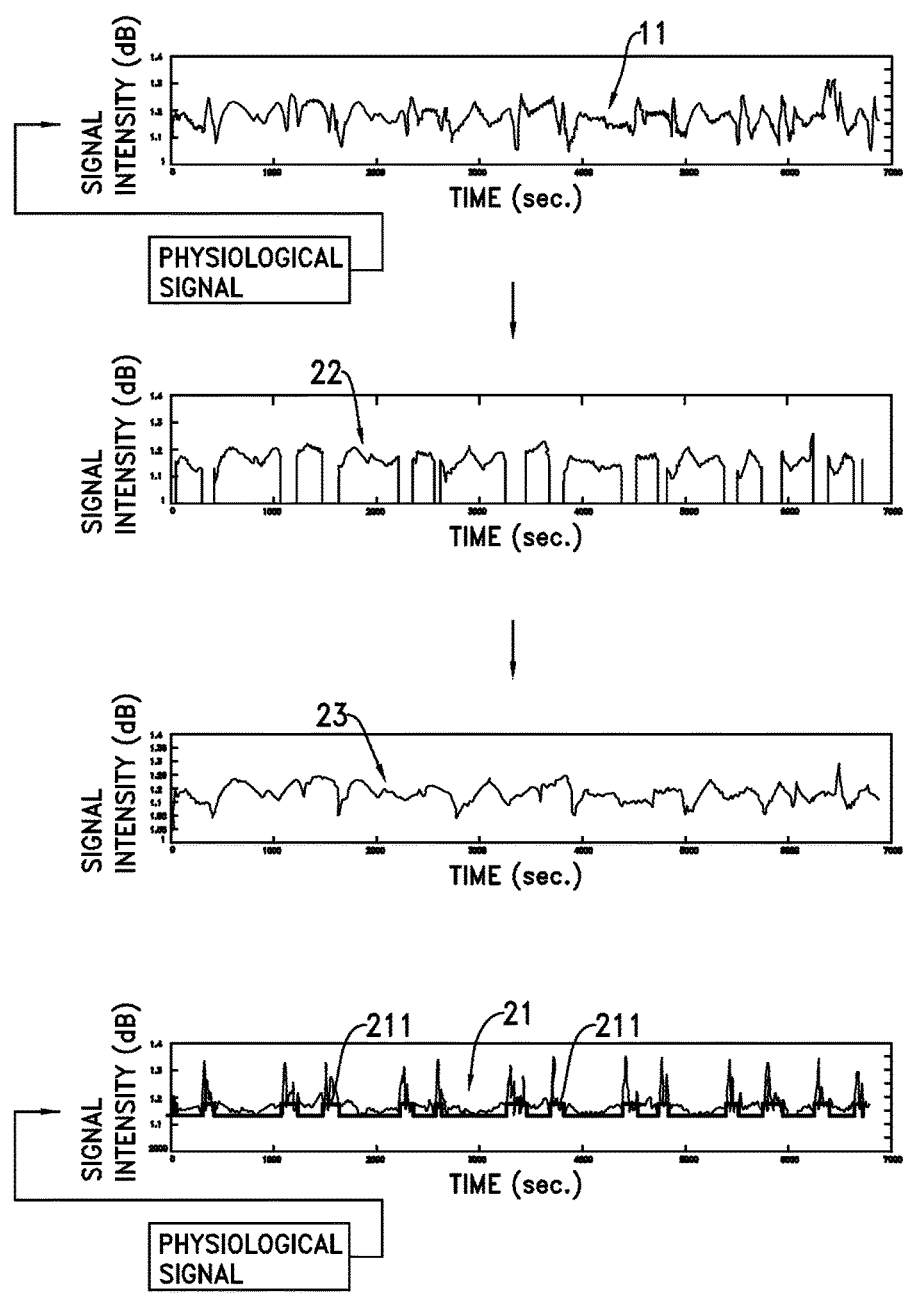
FIG. 5 is a waveform diagram of physiological signals of the physiological signal processing system in FIG. 1 after noise removal and signal compensation.

With Reference to FIG. 5, the processor of the filtering device 20 acquires the information 211 in the corresponding time periods with noises generated therein according to the vibrational signal 21. In the present embodiment, the acquisition of the information 211 in the corresponding time periods may be performed by sequentially calculating a mean value of a rate of change in association with the vibrational signal 21, a standard deviation of the rate of change in association with the vibrational signal 21, and a Gaussian distribution acquired according to the mean value and the standard deviation. The information 211 in the corresponding time periods that represents noises can be identified if the rate of change of the information over time of the vibrational signal 21 is greater than or less than one standard deviation. An equation of the standard deviation is given as follows:

$$\sigma = \sqrt{\frac{1}{N} \sum_{i=1}^{N} [G'(t) - \mu]^2}$$

where σ represents the standard deviation of the rate of change associated with the vibrational signal 21;
N represents a quantity of signals;
G'(t) represents a rate of change associated with the vibrational signal 21 combined by the X-axis signal $G_x(t)$, the Y-axis signal $G_y(t)$, and the Z-axis signal $G_z(t)$;

µ represents the mean value of a rate of change associated with the vibrational signal 21.

To increase the processing efficiency of the filtering device 20, what worth mentioning is when determining that the mean value of the vibrational signal 21-or a sum of the information in the corresponding time periods is less than a threshold value, the processor determines that an acquired physiological signal 11 is valid. Alternatively, when determining that the mean value of the vibrational signal 21 is greater than a configured value or the sum of the information in the corresponding time periods is greater than a percentage, such as 50%, of the physiological signal 11, the processor determines that the acquired physiological signal is invalid.

Figure 6:
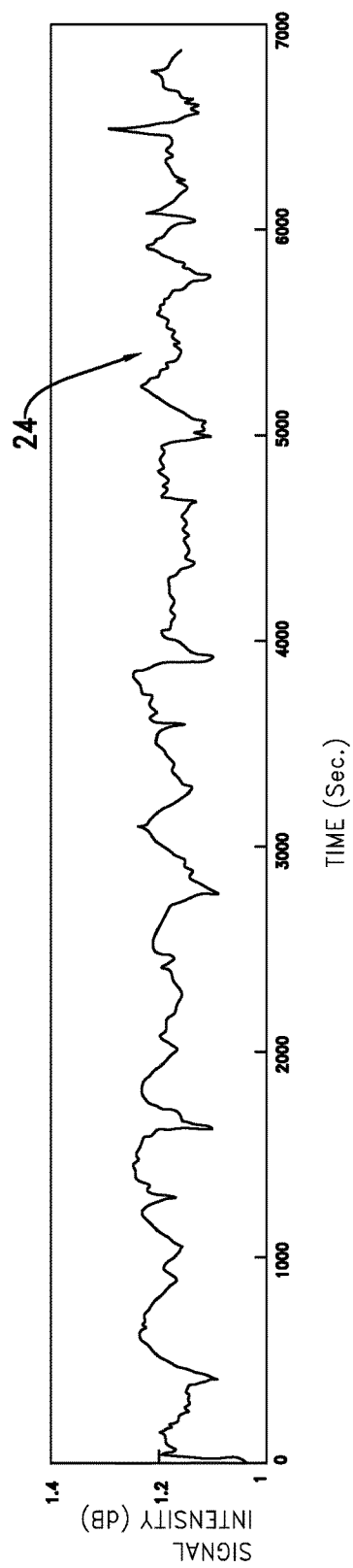
FIG. 6 is a waveform diagram of physiological signals of the physiological signal processing system in FIG. 1 after signal smoothing processing.

Subsequently, the processor of the filtering device 20 further performs the physiological signal filtering algorithm to filter out the noises in the corresponding time periods of the physiological signal 11. In the present embodiment, the way of the processor performing the physiological signal filtering algorithm is done by removing noises in the corresponding time periods from the physiological signal 11. With reference to FIG. 5, a filtered signal 22 is generated and the processor further compensates the filtered signal 22 by connecting breakpoints in the corresponding time periods of the compensated physiological signal in generation of a seamless physiological signal 23. The processor performs a signal smoothing processing algorithm on the seamless physiological signal 23 to generate an output signal 24 as illustrated in FIG. 6. In the present embodiment, the signal smoothing processing algorithm is a linear interpolation or a cubic spline interpolation.

Lastly, the filtering device 20 performs estimation of a physiological parameter indicative of a physiological state of the user according to the compensated output signal 24 for other applications to perform subsequent analyses on the physiological signal. The physiological signal processing system acquires the corresponding time periods 211 of the noises in the vibrational signal 21 through the high-efficiency noise determination algorithm and instantly screens out the noises in the physiological signal to ensure enhanced accuracy of physiological signals.

Figure 7:
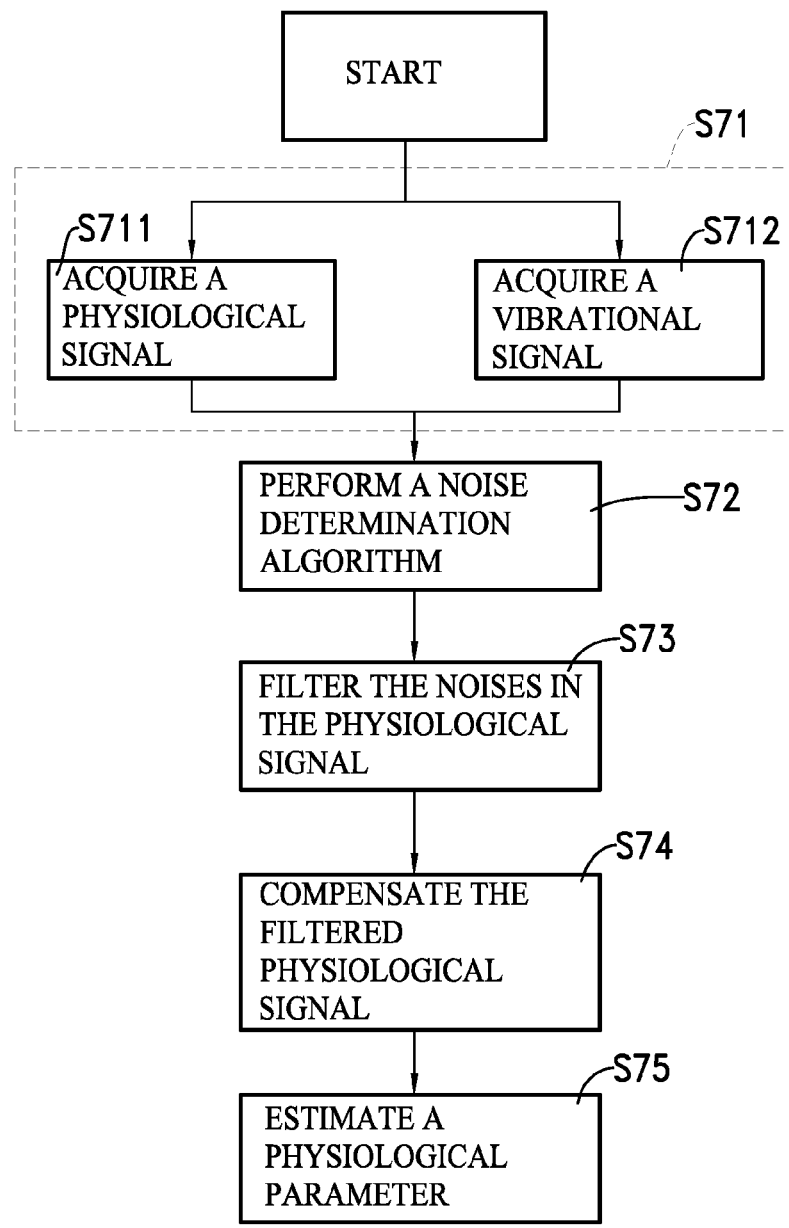
FIG. 7 is a flow diagram of a method for filtering noise generated by the physiological processing system in FIG. 1.

According to the foregoing embodiment and specific applications thereof, a method for filtering noise generated from the foregoing physiological signal processing system can be deduced. The sensing device 10 and the filtering device 20 are connected and the physiological signal processing system performs the method for filtering noise generated by the physiological signal processing system. With reference to FIG. 7, the method for filtering noise generated by the physiological signal processing system includes the following steps.

Step S71: Synchronously receive a physiological signal of a user and a vibrational signal detected by the sensing device 10. Step S71 can be further divided into two steps, namely, step S711 for receiving the physiological signal S711 and step S712 for receiving the vibrational signal 21.

Step S72: Perform a noise determination algorithm to acquire information over time associated with the vibrational signal with noises occurring in corresponding time periods of the vibrational signal 21. In the present embodiment, the way of acquiring the information 211 of the corresponding time periods is to sequentially calculate a mean value of a rate of change in association with the vibrational signal 21, a standard deviation of the rate of change in association with the vibrational signal 21, and a Gaussian distribution acquired according to the mean value and the standard deviation. Noise information 211 in the corresponding time periods can be identified if the rate of change of the information over time of the vibrational signal 21 is greater than or less than one standard deviation.

Step S73: Perform a physiological signal filtering algorithm to filter portions with noises in the corresponding time periods of the physiological signal 11. In the present embodiment, the way of the processor performing the physiological signal filtering algorithm is done by removing noises in the corresponding time periods from the physiological signal 11.

Step S74: Compensate the filtered physiological signal.

Step S75: Estimate the compensated physiological signal to generate a physiological parameter indicative of the user's physiological state according to a result of the signal compensation.

Figure 8:
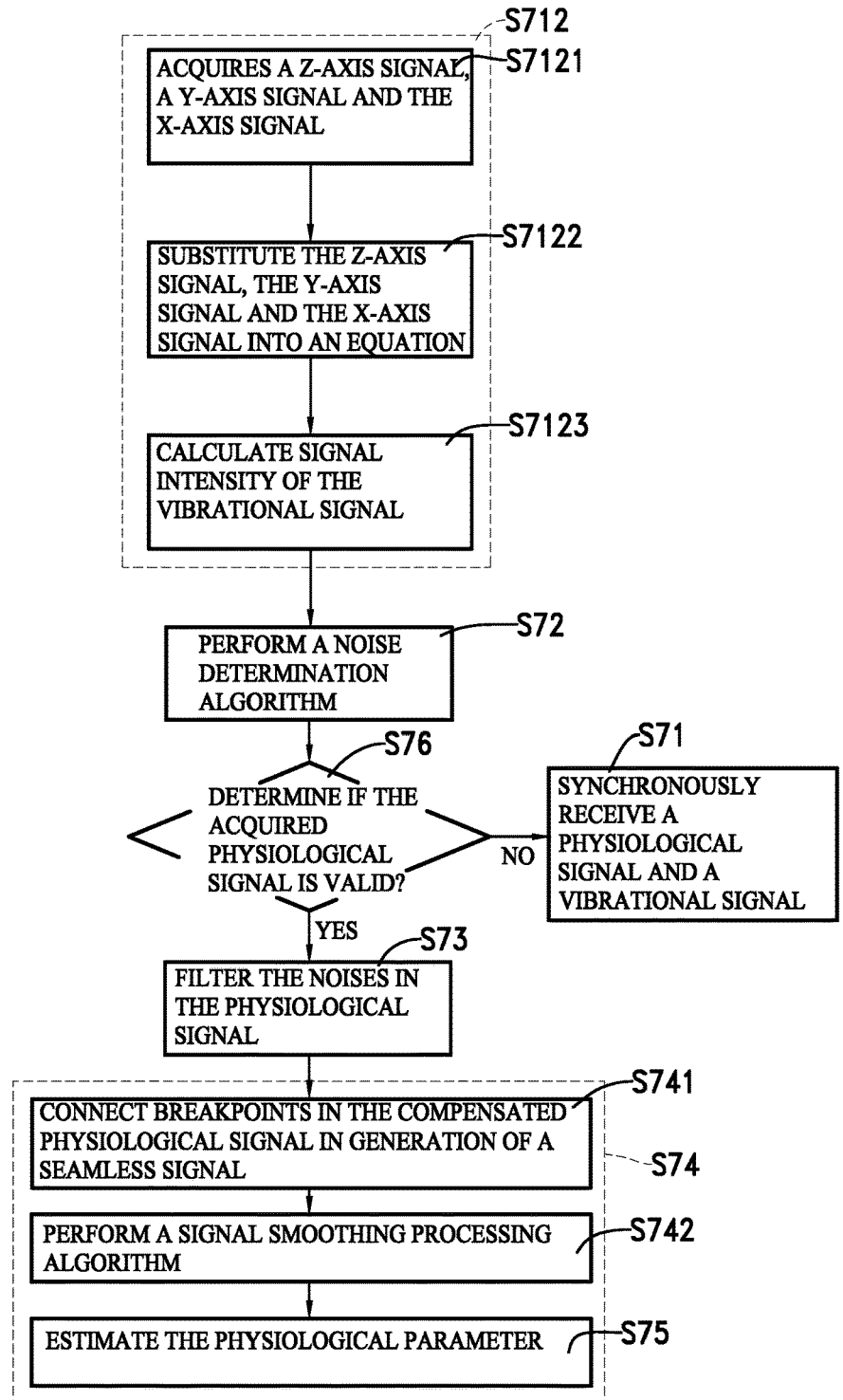
FIG. 8 is a flow diagram of another method for filtering noise generated by the physiological processing system in FIG. 1.

Moreover, with reference to FIG. 8, step S712 for acquiring the vibrational signal further includes the following steps.

Step S7121: Acquire a Z-axis signal 121, a Y-axis signal 122 and an X-axis signal 123 using the filtering device 20.

Step S7122: Substitute the Z-axis signal 121, the Y-axis signal 122 and the X-axis signal 123 into $G_x(t)$, $G_y(t)$ and $G_z(t)$ in the equation $$G(t)=\sqrt{G_x(t)^2 G_y(t)^2+G_z(t)^2}.$$

Step S7123: Calculate signal intensity of the vibrational signal 21, which is a time function associated with signal intensity, such as $G(t)$.

After step S72 for performing a noise determination algorithm to acquire the information over time associated with the vibrational signal 21 with noises occurring in corresponding time periods of the vibrational signal 21, the method further includes the following steps.

Step S76: Determine if the acquired physiological signal 11 is valid according to the vibrational signal 21 or the information 211 in the corresponding time periods. If the determination result is positive, resume step S73. Otherwise, resume step S71.

Given the foregoing steps, the acquired physiological signal 11 can be effectively screened and selected to avoid unnecessary computations performed by the processor. In the present embodiment, step S76 further includes a step of determining if the mean value of the vibrational signal 21 or a sum of the information 211 in the corresponding time periods is less than a threshold value or determining if the mean value of the vibrational signal 21 is greater than a configured value or the sum of the information in the corresponding time periods is greater than a percentage of the physiological signal 11, such as 50%, of the physiological signal. Step S74 for compensating the filtered physiological signal further includes the following steps.

Step S741: Connect breakpoints in the corresponding time periods of the compensated physiological signal in generation of a seamless physiological signal 23.

Step S742: Perform a signal smoothing processing algorithm on the seamless physiological signal 23 to generate an output signal 24.

Lastly, perform step S75 for estimating the compensated physiological signal to generate a physiological parameter indicative of the user's physiological state according to a result of the signal compensation (or the output signal 24). For example, the output signal is analyzed to acquire a physiological parameter associated with Heart Rate Variability (HRV) of the user. In the present embodiment, the signal smoothing processing algorithm is a linear interpolation or a cubic spline interpolation.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A physiological signal processing method for filtering noise generated by a physiological signal processing system, wherein the physiological signal processing system has a sensing device and a filtering device in connection with the sensing device, the method comprising steps of:
   synchronously receiving a physiological signal and a vibrational signal detected by the sensing device;
   performing a noise determination algorithm to acquire information over time associated with the vibrational signal with noises occurring in corresponding time periods of the vibrational signal;
   performing a physiological signal filtering algorithm to filter out portions with noises in the corresponding time periods of the physiological signal and compensate the filtered physiological signal; and
   estimating the compensated physiological signal to generate a physiological parameter according to a result of the signal compensation.

2. The method as claimed in claim 1, wherein in the step of performing the noise determination algorithm, the noises occurring in the multiple time periods are determined by calculating a mean value of a rate of change in association with the vibrational signal and a standard deviation of the rate of change in association with the vibrational signal.

3. The method as claimed in claim 1, wherein the step of receiving the physiological signal and the vibrational signal further has steps of:
   acquiring a Z-axis signal, a Y-axis signal and an X-axis signal;
   calculating a magnitude of the vibrational signal being a time function with an intensity according to the Z-axis signal, the Y-axis signal and the X-axis signal.

4. The method as claimed in claim 1, wherein the step of performing the noise determination algorithm further has steps of:
   determining if the acquired physiological signal is valid according to one of the vibrational signal and the information in the multiple time periods;
   when the determination result is positive, performing the step of performing the physiological signal filtering algorithm to filter the noises in the corresponding time periods of the physiological signal; and
   when the determination result is negative, performing the step of synchronously receiving the physiological signal and the vibrational signal.

5. The method as claimed in claim 4, wherein the step of determining if the acquired physiological signal is valid according to one of the vibrational signal and the information in the corresponding time periods further has a step of determining if a mean value of the vibrational signal is greater than a configured value.

6. The method as claimed in claim 4, wherein the step of determining if the acquired physiological signal is valid according to one of the vibrational signal and the information in the corresponding time periods further has a step of determining if a sum of the information in the corresponding time periods of the vibrational signal is greater than a percentage of the physiological signal.

7. The method as claimed in claim 1, wherein the step of performing the physiological signal filtering algorithm further has steps of:
   connecting breakpoints in the corresponding time periods of the compensated physiological signal in generation of a seamless physiological signal; and
   performing a signal smoothing processing algorithm on the seamless physiological signal to generate an output signal indicative of the physiological parameter.

8. A physiological signal processing system, comprising:
   a sensing device serving to synchronously detect a physiological signal and a vibrational signal; and
   a filtering device connected to the sensing device and having a processor performing a method for filtering the noises generated by the physiological signal processing system;
   wherein the method comprises steps of:
   synchronously receiving the physiological signal and the vibrational signal detected by the sensing device;
   performing a noise determination algorithm to acquire information over time associated with the vibrational signal with noises occurring in corresponding time periods of the vibrational signal;
   performing a physiological signal filtering algorithm to filter out portions with noises in the corresponding time periods of the physiological signal and compensate the filtered physiological signal; and
   estimating the compensated physiological signal to generate a physiological parameter according to a result of the signal compensation.

9. The physiological signal processing system as claimed in claim 8, wherein the sensing device and filtering device are connected through one of wireline connection and wireless connection, the filtering device is connected to the sensing device according to a communication protocol, the communication protocol is one of a Bluetooth® protocol, a WiFi® (Wireless Fidelity) protocol and an RFID® (Radio Frequency Identification) protocol, the sensing device is one of a wearable smart watch and an optical physiological state detection watch, and the filtering device is one of a smart mobile device and a smart vehicular computer.

* * * * *